United States Patent
Kim

(10) Patent No.: US 9,314,476 B2
(45) Date of Patent: Apr. 19, 2016

(54) COMPOSITION FOR TREATING OR PREVENTING NEURODEGENERATIVE BRAIN DISEASES COMPRISING BLACK BEAN EXTRACT

(75) Inventor: Myeong Ok Kim, Gyeongsangnam-do (KR)

(73) Assignee: Industry-Academic Cooperation Foundation Gyeongsang National University, Gyeongsangnam-do (KR)

( * ) Notice: Subject to any disclaimer, the term of this patent is extended or adjusted under 35 U.S.C. 154(b) by 0 days.

(21) Appl. No.: 13/640,193

(22) PCT Filed: Apr. 7, 2011

(86) PCT No.: PCT/KR2011/002451
§ 371 (c)(1),
(2), (4) Date: Jan. 11, 2013

(87) PCT Pub. No.: WO2011/126322
PCT Pub. Date: Oct. 13, 2011

(65) Prior Publication Data
US 2013/0109640 A1    May 2, 2013

(30) Foreign Application Priority Data
Apr. 9, 2010  (KR) .................. 10-2010-0032869

(51) Int. Cl.
*A61K 31/7048* (2006.01)
*A61K 36/48* (2006.01)

(52) U.S. Cl.
CPC ............. *A61K 31/7048* (2013.01); *A61K 36/48* (2013.01)

(58) Field of Classification Search
CPC .................................................. A61K 31/7048
See application file for complete search history.

(56) References Cited

U.S. PATENT DOCUMENTS

2008/0292607 A1    11/2008   Mazzio et al.

FOREIGN PATENT DOCUMENTS

| KR | 100509440 | B1 |   | 8/2005  |
|----|-----------|----|---|---------|
| KR | 100733913 | B1 |   | 6/2007  |
| KR | 10-0785466|    | * | 12/2007 |
| KR | 100785466 | B1 |   | 12/2007 |

OTHER PUBLICATIONS

Shih, et al.; 2010; "Antioxidant and cognitive promotion effects of anthocyanin-rich mulberry (*Morus atropupurea* L.) on senescence-accelerated mice and prevention of Alzheimer's disease"; Journal of Nutritional Biochemistry; 21: 598-605.

Shinomiya, et al.; 2005; "Effect of Seed Coat Extract From Black Soybeans on Radial Maze Performance in Rats"; Clinical and Experimental Pharmacology and Physiology; 32: 757-760.

* cited by examiner

*Primary Examiner* — Bahar Craigo
(74) *Attorney, Agent, or Firm* — Cesari and McKenna LLP

(57) ABSTRACT

The present invention relates to a composition for treating or preventing neurodegenerative brain diseases comprising a black bean extract, and more particularly, to a composition for treating or preventing neurodegenerative brain diseases comprising a black bean extract or a fraction thereof, which comprises 15-25 wt % of delphinidin-3-glucoside, 65-80 wt % of cyanidin-3-glucoside and 5-10 wt % of petunidin-3-glucoside, a functional food composition for enhancing brain or cognitive function comprising the black bean extract or a fraction thereof, and a method for preparing the composition.

9 Claims, 17 Drawing Sheets

R$_1$=R$_2$=R$_3$=OH     Delphinidin-3-glucoside (DG)
R$_1$=R$_2$=OH, R$_3$=H   Cyanidin-3-glucoside (CG)
R$_1$=OMe, R$_2$=R$_3$=OH  Petunidin-3-glucoside (PG)

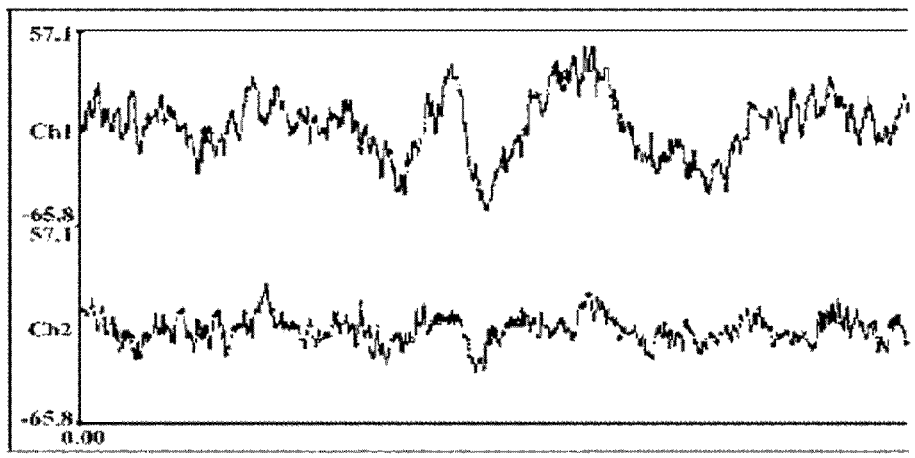
Electroencephalogram of normal group
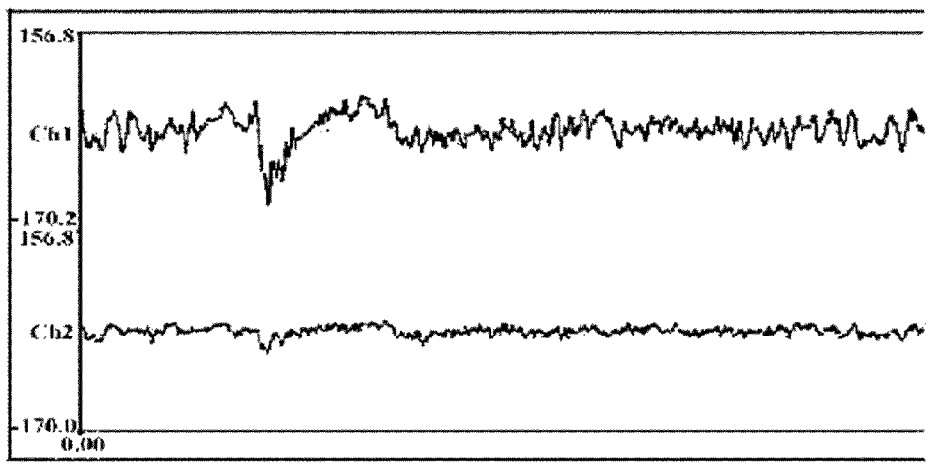
Electroencephalogram of dementia-induced test group

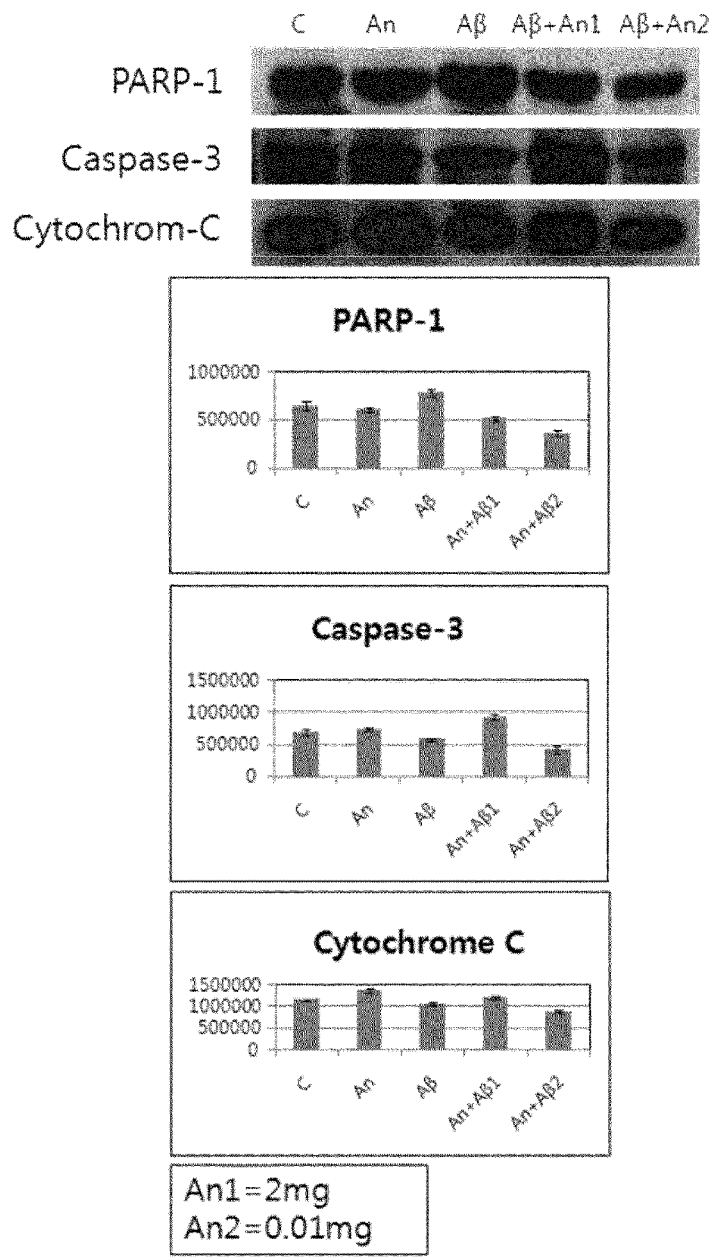

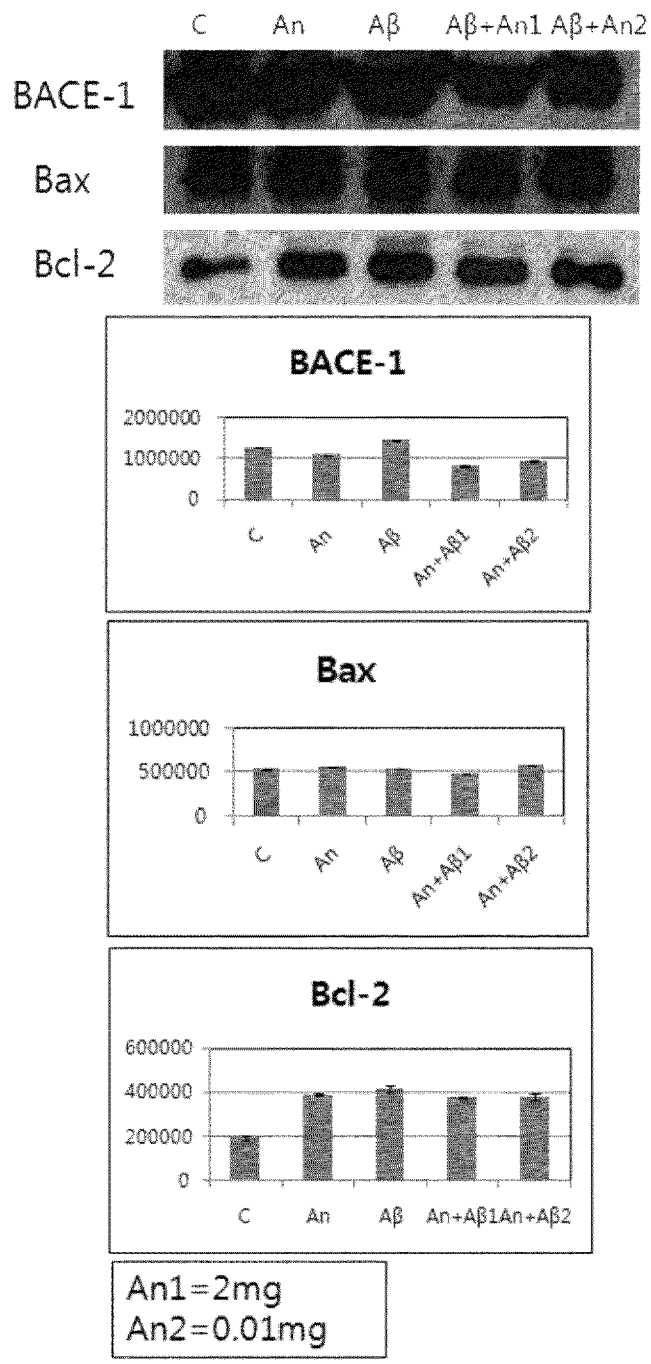

COMPOSITION FOR TREATING OR PREVENTING NEURODEGENERATIVE BRAIN DISEASES COMPRISING BLACK BEAN EXTRACT

CROSS REFERENCE TO RELATED APPLICATIONS

The present application is a national phase application under 35 U.S.C. §371 of PCT International Application No. PCT/KR2011/002451, filed on Apr. 7, 2011, which claims the benefit of Korean Patent Application No. 10-2010-0032869, filed on Apr. 9, 2010, each of which are herein incorporated by reference in its entirety.

TECHNICAL FIELD

The present invention relates to a composition for treating or preventing neurodegenerative brain diseases comprising a black bean extract, and more particularly, to a composition for treating or preventing neurodegenerative brain diseases comprising a black bean extract or a fraction thereof, which comprises 15-25 wt % of delphinidin-3-glucoside, 65-80 wt % of cyanidin-3-glucoside and 5-10 wt % of petunidin-3-glucoside, a functional food composition for enhancing brain or cognitive function comprising the black bean extract or a fraction thereof, and a method for preparing the composition.

BACKGROUND ART

The rapid development of lifescience and medicine has increased the average life expectancy of humans, and a gradual increase in the number of the aging population is creating new social problems. Particularly, age-related neurodegenerative diseases including strokes, Alzheimer's disease (AD) and Parkinson's disease (PD), can appear as fatal nervous dysfunctions. Under current circumstances, there is no effective method capable of preventing these diseases, and thus these diseases reduce quality of life, cause a large amount of medical expenses, and impose a significant burden on the patient's family. Due to the severity of such problems, efforts to overcome these diseases have been made worldwide. For example, the United States announced the Decade of the Brain on Jan. 1, 1990, and Japan has announced the Century of the Brain. In addition, South Korea established Braintech 21 in 1998.

Alzheimer's disease develops in 2% of elderly who are 60 years old, and medical technology is spreading to underdeveloped countries. However, due to an increase in the aging population, about 20,030,000 Alzheimer's patients in the year 2025 are expected to exist (http://www.alz.co.uk/). In the case of stroke, it is estimated that about 15,000,000 will occur in the year 2025. In the USA, in the year 1997, 4,000,000 AD patients and 3,000,000 stoke patients were diagnosed and incurred about $1,300. Based on this, it is estimated that medical expenses caused by the above two diseases are about $4,000 (520 trillion won) in the year 2003. In Korea, brain diseases occurring in old people are major causes of death and will place financial strain on the development of the national economy and the national health service.

Alzheimer's disease (hereinafter referred to as AD) is a brain nerve disease that is the most common form of dementia, and accounts for 70% of dementia cases and results in the loss of cognitive ability due to the progressive degeneration of nerve cells. In AD, brain portions that are involved in attention, memory and language functions are damaged, so that memory is lost, consciousness becomes unclear, and cerebral functions, including thinking, calculation, discernment and common sense are impaired, making occupational and social activities difficult.

The brain of patients who die of AD is pathologically characterized by senile plaques and neurofibrillary tangles. The senile plaques are formed by the extracellular accumulations of proteins and dead cells, and the major component thereof is β-amyloid peptide. Also, the major component of the neurofibrillary tangles is tau protein. The tau protein functions as a structure that strengthens nerve cells in the central nervous system. However, in the brain of dementia patients, this tau protein is chemically altered to form tangles. For this reason the tau protein disrupts communication between nerve cells, resulting in nerve cell death.

Studies associated with AD to date resulted in the development of preventive and therapeutic agents for AD mainly using agents inhibiting beta-amyloid production and inhibitors of neurotoxicity, such as antioxidants. Current medications for AD include nicotinic receptor agonists, such as ABT-418; muscarinic receptor agonists, such as Xanomeline and YM-976; acetylcholine precursors, such as lecithin and acetyl-L-carnitine; metal chelators, such as desferrioxamine and lioquinol; beta-sheet breakers, such as iAβ5 and iAβ11; antioxidants, such as vitamin E, *Ginkgo biloba*, melatonin and idebenone; sAPP releasing agents, such as nicotine, acetylcholine and carbachol; β-secretase or γ-secretase inhibitors, such as OM99-1, OM99-2, OM99-3 and Z-VLL-CHO; non-steroidal anti-inflammatory drugs (NSAIDs), such as ibuprofen and indomethacin; hormones such as estrogen; vaccines, such as AN-1792; and cholesterol-lowering agents, such as simvastatin and atorvastatin. However, most medications are only marginally helpful in slightly relieving the pathological symptoms of AD or slowing AD progression, or are difficult to apply in practice due to their toxicity. Thus, there remains an urgent need for the development of stable and effective drugs for AD treatment. Recent AD-associated studies have been focused on the identification of the neurotoxic mechanisms of beta-amyloid. Pro-apoptotic genes, such as prostate apoptosis response-4 (Par-4), tau protein kinase 1 (GSK-3β), Calsenilin/DREAM/KChIP3, and cell death-promoting gene 5 (DP5), are shown to be overexpressed or their activities are increased in neuronal cells cultured in the presence of beta-amyloid or neuronal cells from AD patients. The blocking of the functions of the proteins reduces beta-amyloid-induced neuronal death. However, these reports are not sufficient to identify an intracellular signaling pathway for beta-amyloid-induced neuronal toxicity so as to develop AD drugs for preventing beta-amyloid-induced neuronal loss.

Meanwhile, Korean Patent Laid-Open Publication No. 99-85202 discloses a ginseng-based product obtained by mixing several kinds of herbs and extracting the mixture. However, because this product is based on a ginseng component, it can cause adverse effects such as palpitations or homeostasis imbalance in hypertension patients. Thus, in the case of conventional compositions for dementia treatment, the adverse effects thereof become the biggest problem, and particularly, herbal medicinal preparations have significantly less adverse effects compared to other medications, but can cause other adverse effects in some cases. Thus, there is an urgent need for the development of a composition which causes no adverse effects.

The present inventors have made extensive efforts to find plants and extracts thereof having no adverse effects and, as a result, have paid attention to black beans. Anthocyanin contained in black beans is a common substance in higher plants and cause colors to be shown in flowers and fruits and also belongs to the family of flavonoids which are pigments found in plant vacuoles. Anthocyanin appears red, purple or green depending on the pH of plants. It is known to protect plant cells from UV rays and insect invasion. Free oxygen radicals are generated by a process in which food is metabolized in the human body. The generated free oxygen radicals react with cell molecules in vivo to oxidize cells. As is well known in the art, when cells are oxidized, the cells are broken down to cause various diseases or to cause cancer by DNA denaturation. Antioxidants bind to free oxygen radicals to prevent cell oxidation and have antioxidant activity.

Known antioxidants include vitamin C, vitamin E, beta-carotene and the like, and in recent years, anthocyanin has received attention as a potent antioxidant in the medical world. Plants known to have anthocyanin include purple carrots, cranberries, blueberries and the like, but the effects of anthocyanin on the improvement of memory and the amelioration of dementia have not yet been known.

Accordingly, the present inventors have made extensive efforts to find a substance effective in improving memory and ameliorating dementia without side effects and, as a result, have found that an anthocyanin component extracted from black beans inhibits and reduces the accumulation of BACE-1 enzyme which is involved in the formation of β-amyloid protein found in the brain of rats having Alzheimer's disease induced by administration of β-amyloid, suggesting that it is effective in treating or ameliorating neurodegenerative brain diseases, thereby completing the present invention.

DISCLOSURE

Technical Problem

It is an object of the present invention to provide a composition effective in preventing or treating neurodegenerative brain diseases by reducing the accumulation of beta-amyloid, comprising a black bean extract or a fraction thereof, which comprises 15-25 wt % of delphinidin-3-O-glucoside, 65-80 wt % of cyanidin-3-O-glucoside and 5-10 wt % of petunidin-3-O-glucoside.

Another object of the present invention is to provide a functional food composition for enhancing brain or cognitive function, comprising a black bean extract or a fraction thereof, which comprises 15-25 wt % of delphinidin-3-glucoside, 65-80 wt % of cyanidin-3-glucoside and 5-10 wt % of petunidin-3-glucoside.

Still another object of the present invention is to provide a method for preparing the above composition for preventing or treating neurodegenerative brain diseases, comprising: a) extracting a black bean with water, an organic solvent or a mixed solvent thereof to obtain a black bean extract; b) fractionating the obtained extract with water or a non-polar organic solvent to obtain a fraction; and c) isolating and purifying delphinidin-3-gluco side, cyanidin-glucoside and petunidin-3-glucoside from the fraction.

Technical Solution

In order to accomplish the above objects, in one aspect, the present invention provides a composition for preventing or treating neurodegenerative brain diseases, comprising a black bean extract or a fraction thereof, which comprises 15-25 wt % of delphinidin-3-glucoside, 65-80 wt of cyanidin-3-glucoside and 5-10 wt % of petunidin-3-glucoside.

The present invention also provides a functional food composition for enhancing brain or cognitive function, comprising a black bean extract or a fraction thereof, which comprises 15-2 wt % of delphinidin-3-glucoside, 65-80 wt % of cyanidin-3-glucoside and 5-1.0 wt % of petunidin-3-glucoside.

The present invention also provides a method for preparing the above composition for preventing or treating neurodegenerative brain diseases, comprising: a) extracting a black bean with water, an organic solvent or a mixed solvent thereof to obtain a black bean extract; b) fractionating the obtained extract with water or a non-polar organic solvent to obtain a fraction; and c) isolating and purifying delphinidin-3-glucoside, cyanidin-3-glucoside and petunidin-3-glucoside from the fraction.

In the present invention, the black bean extract may be obtained by washing, drying and crushing a black bean hull and extracting the crushed black bean hull with water, and organic solvent or a mixed solvent thereof. The black bean extract is prepared by extraction with a solvent selected from the group consisting of water, a C1-C4 lower alcohol and a mixed solvent thereof. Preferably, it is prepared by extraction with methanol or ethanol. More preferably, it is prepared by extraction with methanol.

In the present invention, the extract includes any one of an extract resulting from extraction, a dilution of the extract, a concentrate of the extract, a dried material obtained by drying the extract, a crude extract, and a purified extract.

In one embodiment of the present invention, the black bean extract is extracted with a 1% HCl-MeOH solvent, and the extract is passed through cation exchange resin such as Amberlite XAD 7 to separate an anthocyanin-containing cationic compound from a nonionic compound. Then, to remove nonionic water-soluble and non-polar substances, the cationic compound is eluted in 1% HCl-MeOH, thereby obtaining an anthocyanin-containing ionic compound. In the second step, the compound is subjected to size exclusion chromatography using a column packed with Sephadex LH20 in 1% HCl-MeOH/water-solvent, and then purified by reverse-phase chromatography using a C18 Sep Pak column, thereby obtaining an anthocyanin-based compound effective in treating or preventing neurodegenerative brain diseases.

The black bean extract can be prepared from various natural and hybrid species and various organs. In a specific embodiment of the present invention, a black bean extract is prepared by adding methanol or ethanol to the soybean cultivar "core-green Geomjeongkong #1", collecting and concentrating the supernatant and freeze-drying the concentrate.

In addition, a solvent fraction may also be obtained by suspending the alcohol concentrate in water and fractionating the suspension with a non-polar solvent such as n-hexane, chloroform or ethylacetate.

Further, the solvent fraction may be purified by Sephadex column chromatography using, as a mobile phase, a mixed solvent of two or more selected from among polar solvents, including methanol, ethanol, propanol or isopropanol, and non-polar solvents, including ethylacetate, n-hexane, dichloromethane or chloroform, thereby obtaining an anthocyanin compound effective in preventing or treating neurodegenerative brain diseases.

Advantageous Effects

The inventive composition comprising antocyanins extracted from black beans has the effects of inhibiting neuronal cell death induced by aging and beta-amyloid in the cortex and hippocampus of the brain, and of regenerating neuronal cells. Thus, it can be used as a pharmaceutical composition or food composition for treating or preventing neurodegenerative brain diseases.

DESCRIPTION OF DRAWINGS

FIG. 2b shows the results of measuring amplified signals at 250 Hz in order to select animals having Alzheimer's disease induced by injection of beta-amyloid and shows a comparison of an electroencephalogram between a normal group and a test group having dementia induced by injection of beta-amyloid.

FIG. 6c shows the results of examining the changes in PARP-1, caspase-3 and cytocrom-C proteins involved in cell death in the hippocampus of dementia-induced rats as a function of the concentration of anthocyanins administered. It was observed that cell death was much more inhibited in the group administered with 2 mg of anthocyanins.

FIG. 6d shows the results of examining the changes in Bax, Bcl-2 and BACE-1 proteins involved in cell death in the hippocampus of dementia-induced rats as a function of the concentration of anthocyanins administered. It was observed that cell death was much more inhibited in the group administered with 2 mg of anthocyanins.

MODE FOR INVENTION

Figure 1:
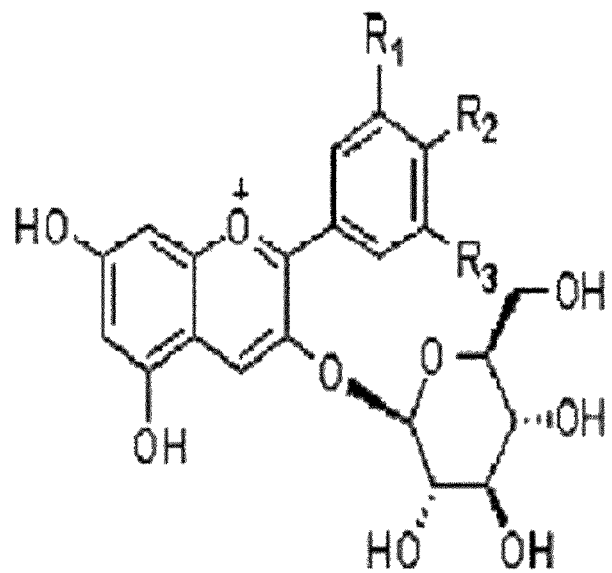
FIG. 1 shows the structures of delphinidin-3-O-glucoside, cyanidin-3-O-glucoside and petunidin-3-O-glucoside, which are anthocyanins extracted in the present invention.

Hereinafter, the present invention will be described in detail.

As used herein, the term "black bean" is called Komjungkong or Heuk-dae-doo in Korean. The names collectively designate blackish beans rather than designating a certain kind of bean. The black bean contains a large amount of anti-aging components and is effective in preventing adult diseases and promoting weight loss, compared to other general beans, and examples thereof include Heuk-tae, Seo-ri-tae and Seo-mok-tae in Korean. Heuk-tae has the largest size among black beans and is used in bean-mixed rice or black beans in sauce. Seo-ri-tae is blackish but has a green core, and it is used in Kongtteok in Korean, black beans in sauce or bean-mixed rice. Seo-mok-tae (Rhynchosia Nolubilis) looks small like the rat's eye and is used as a Chinese medicine. Preferably, the black bean that is used in the present invention may be the soybean cultivar "Core-Green Geomjeongkong #1", which has a high content of anthocyanin compared to general beans and thus makes it easy to separate anthocyanin according to the present invention.

As used herein, the term "soybean cultivar core-green Geomjeongkong #1" refers to a variety by professor Jong-Il JUNG, College of Agriculture and Life Science, Gyeongsang National University and is free of the Kunitz trypsin inhibitor (a protein that causes bean allergy and inhibits digestion) and lipoxygenase (which causes a beany taste). It is a kind of Seo-ri-tae that can be reproduced.

The soybean cultivar "Core-Green Geomjeongkong #1" is a cultivar developed with traditional genetic breeding techniques, including crossing and selection of characters, without using genetic manipulation. Thus, it is harmless to the human body and can provide various bean products which are discriminated from genetically modified beans or imported beans.

As used herein, the term "anthocyanin" refers to a component which is present mainly in colorful portions in the flower of plants or the peel of fruits and mainly shows red, blue, purple or the like. It is a compound having ether-type bonds between a hydroxyl group and various functional groups such as alcohol, phenol and aldehyde. It changes to red when acid is added, and it is quickly discolored. It is known that the reason why flowers show various beautiful colors is that anthocyanin forms various complexes metal salts such as potassium or magnesium in plants.

In the case of grape skin which is most frequently used as a source for extraction of anthocyanin, 330-6,030 mg of anthocyanin can be extracted, suggesting that the amount of anthocyanin that can be extracted from black bean hulls is at least two times larger than that from grape skins. In comparing black beans and grapes, black beans are in a dried state, whereas grapes generally have a water content of about 80%. When the content of anthocyanin is compared between black bean hulls and dried grape skins, the weight of raw grape skins required to produce 1 kg of: dried grape skins is 28 kg, and the theoretical content of anthocyanin that can be obtained therefrom is 30,139 mg or less, while 37,330 mg of anthocyanin can be obtained from 28 kg of black bean hulls. Thus, the content of anthocyanin in 1 kg of black bean hulls is higher by about 7,000 mg than that in 1 kg of dried grape skins. Further, when anthocyanin is extracted from grape skins, large amounts of sugar components or organic acids are extracted in addition to anthocyanin, and for this reason, the purity of the pigment is reduced and the stability and storage stability of the pigment are reduced by sugars and organic acids. However, black bean hulls consist mostly of insoluble fibers, and thus relatively pure anthocyanin can be extracted therefrom while undesired material is not substantially dissolved, suggesting that black bean hulls are a good source for extraction of anthocyanin.

Preferably, the black bean extract of the present invention may contain various anthocyanin compounds. Most preferably, it may comprise 15-25 wt % of delphinidin-3-O-glucoside, 65-80 wt % of cyanidin-3-O-glucoside and 5-10 wt % of petunidin-3-O-glucoside, which are represented by the following formula:

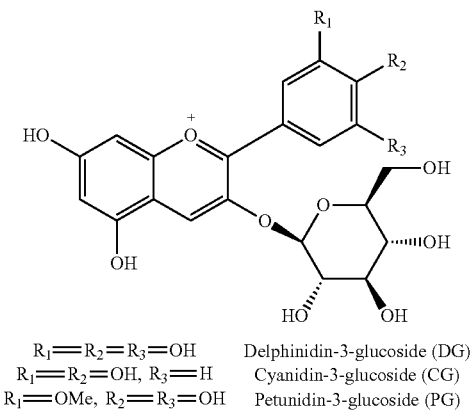

$R_1$=$R_2$=$R_3$=OH    Delphinidin-3-glucoside (DG)
$R_1$=$R_2$=OH, $R_3$=H    Cyanidin-3-glucoside (CG)
$R_1$=OMe, $R_2$=$R_3$=OH    Petunidin-3-glucoside (PG)

In the anthocyanins of the present invention, which comprise the above three components, the number and position of oxygen functional groups (OH or $OCH_3$) substituted on the benzene rings can influence biological activities involved in anti-aging and anti-degeneration. Further, the oxygen functional groups attached to the single benzene ring have high activities, and as the number of the oxygen functional groups increases, the biological activity of the compound increases. This suggests that the biological activities of the anthocyanins of the present invention are increased by the oxygen substituents of the above three compounds, that is, delphinidin-3-O-glucoside, cyanidin-3-O-glucoside and petunidin-3-O-glucoside.

As used herein, the term "neurodegenerative brain diseases" refers to diseases in which degenerative changes occur in the neuronal cells of the central nervous system to cause various symptoms. Typical examples of neurodegenerative brain diseases which can be treated and prevented by the anthocyanins of the present invention include, but are not limited to, Alzheimer's disease, Parkinson's disease, progressive supranuclear palsy, multiple system strophy, olivopontocerebellar atrophy (OPCA), Shy-Drager syndrome, striatonigral degeneration, Huntington's disease, amyotrophic lateral sclerosis (ALS), essential tremor, cortico-basal ganlionic degeneration, Diffuse Lewy body disease, Parkinson-ALS-dementia complex of Guam, and Pick's disease. Preferably, the anthocyanins of the present invention have the effect of treating or ameliorating dementia or Alzheimer's disease.

Dementia, a neurodegenerative brain disease disclosed herein, refers to the loss of cognitive (thinking) ability and social activity to a degree beyond what is expected from normal aging. It is not a specific disease but simply a phrase to collectively refer to a set of symptoms. Dementia can be the symptom caused by various diseases, including diffuse Lewy dementia, dementia due to head trauma. Alzheimer's disease, vascular dementia and diffuse Lewy dementia only show its symptom with dementia. Diseases causing dementia commonly show conditions of dementia, and in this case, dementia can be easily diagnosed by examining conditions other than dementia.

Alzheimer's disease is the most typical form of dementia. Alzheimer's disease shows abnormal plaques and neurofibrillary tangles in nerve cells. In addition, Alzheimer's disease is characterized by a significant loss of brain nerve cells important in maintaining memory and other thinking abilities and a significant decrease in the amount of a specific chemical substance required for the complex signaling between brain nerve cells. The first symptom of Alzheimer's disease is forgetfulness followed by impairments in language, cognition, reading and writing abilities, etc. Patients with Alzheimer's disease can be anxious, can be very aggressive and are likely to be disoriented by time and place.

The cause of Alzheimer's disease-type dementia (in which brain cells die rapidly to cause brain atrophy) has not yet been found and the relationship of the disease with anthocyanins is not yet clear. However, it is believed that antocyanins present in black beans in large amounts function to remove free oxygen radicals in the brain and prevent a decrease in acetylcholine, thereby preventing the aging of nerve cells. Thus, antocyanins are useful against neurodegenerative brain diseases.

In one Example of the present invention, it was found that, in beta-amyloid-induced Alzheimer's disease, BACE-1 protein and Bax/Bcl-2 were reduced, suggesting that anthocyanins have the effect of inhibiting nerve cell death, and thus can be used to treat Alzheimer's disease (FIGS. 5 and 6).

In the present invention, the neurodegenerative brain diseases may be diseases induced by the accumulation of beta-amyloid protein in brain cells.

As used herein, the term "β-amyloid" refers to a protein produced from amyloid precursor protein by the action of AD-specific protease. It is known that beta-amyloid is deposited in brain tissue to cause brain cell death. If cerebral nerve cells involved in functions such as memory are degenerated to die in large amounts, fiber-shaped structures, called "age spots" or "neurofibril changes" appear in nerve cells. It is known that nerve cells in Alzheimer's disease patients are killed by cell death mechanisms. Preferably, it was found that anthocyanin-based compounds separated according to the present invention have the effect of reducing the expression level of the dementia-inducing beta-amyloid (Aβ) protein in brain cells having the protein deposited therein. In addition, it was shown that the anthocyanin-based compounds inhibit the expression of Bax protein inducing cell death and induce the expression of Bcl-2 protein inhibiting cell death, thereby inducing the death of Aβ-deposited brain cells.

In one preferred embodiment of the present invention, the black bean extract of the present invention can be used to treat or prevent neurodegenerative brain diseases by protecting nerve cells, and this treatment or prevention can be achieved by inhibiting the death of nerve cells. In one embodiment of the present invention, the black bean extract of the present invention comprises 15-25 wt % of delphinidin3-O-glucoside, 65-80 wt % of cyanidin-3-O-glucoside and 5-10 wt % of petunidin-3-O-glucoside. It was shown that the black bean extract inhibits neuronal cell death in a beta-amyloid-induced Alzheimer's disease model or aged rats with natural degenerative disease (FIGS. 5 to 9).

The composition of the present invention may further comprise a pharmaceutically acceptable carrier. As used herein, the term "pharmaceutically acceptable" refers to a composition that is physiologically acceptable and does not cause gastric disorder, allergic reactions such as gastrointestinal disorder or vertigo, or similar reactions, when administered to humans. Examples of pharmaceutically acceptable carriers include carriers for oral administration, lactose, starch, cellulose derivatives, magnesium stearate, and stearic acid, and carriers for parenteral administration, such as water, suitable oils, saline solution, aqueous glucose and glycol. The composition of the present invention may further comprise stabilizers and preservatives. Suitable stabilizers include antioxidants, such as sodium hydrogen sulfite, sodium bisulfite or ascorbic acid. Suitable preservatives include benzalkonium chloride, methyl- or propyl-paraben, and chlorobutanol. For other pharmaceutically acceptable carriers, reference may be made to Remington's Pharmaceutical Sciences, $19^{th}$ ed., Mack Publishing Company, Easton, Pa., 1995. The pharmaceutical composition of the present invention can be formulated into suitable forms with the above-described pharmaceutically acceptable carriers according to any method known in the art. Specifically, the pharmaceutical composition can be formulated into various parenteral or oral dosage forms. Typical formulations for parenteral administration include injectable formulations, preferably an isotonic aqueous solution or a suspension. The injectable formulation can be prepared using a suitable dispersing agent, wetting agent or suspending agent according to any technique known in the art. For example, the injectable formulation can be prepared by dissolving each component in saline or buffer. In addition, formulations for oral administration include, but are not limited to, powders, granules, tablets, pills and capsules.

The pharmaceutical composition formulated as described above as described above may be administered in an effective amount through various routes, including oral, transdermal, subcutaneous, intravenous and intramuscular routes. As used herein, the term "effective amount" refers to the amount of the composition which shows a preventive or therapeutic effect when administered to a patient.

The dose of the pharmaceutical composition of the present invention may be suitably selected depending on the route of administration, the subject to be administered, and the age, sex, body weight, characteristic and disease condition of the subject. More preferably, the composition may be administered orally at a dose of 0.48 mg/kg/day.

According to the following method, the present inventors have found that the composition of the present invention has the effect of preventing or treating neurodegenerative brain diseases. Specifically, anthocyanin-based compounds separated from black beans were purified, and rats having Alzheimer's disease induced by administering beta-amyloid were divided into a test group and a control group, and normal aged rats were also used. For selection of Alzheimer's disease-induced animals from the two groups, amplified signals were measured at 250 Hz with reference to the method of R. Ganguly and D. Guha (2008; EEG wave). The inventive composition comprising the anthocyanin compounds was administered to the test group for 40 days, after which the degree of neuronal cell death, the changes in PARP-1, caspase-3 and cytochrome-c proteins involved in cell death and the expression levels of BACE-1, Bax and Bcl-2 proteins were examined, and the tissue was immunostained. In addition, the cytotoxicity of HT22 cells was analyzed by an MTT assay, and the change in the mitochondrial membrane was analyzed by JC-1. As a result, in the group administered with the inventive composition comprising the anthocyanin compounds, the inhibition of neuronal cell death and the decrease in the expression of BACE-1 protein were observed. Also, the expression of Bax protein functioning to induce cell death in the rat brain having beta-amyloid deposited therein was reduced and the expression of Bcl-2 protein was increased. This suggests that the composition of the present invention was effective in inhibiting the death of neuronal cells in the brains of the dementia-induced rats and the normal aged rats. Further, it could be seen that, in the group administered with higher concentrations of the anthocyanins, cell death was much more inhibited. Also, the results of the MTT assay indicated that the group treated with the anthocyanins showed decreased cytotoxicity. In addition, the results of the JC-1 assay indicated that, in the group treated with the anthocyanins, the change in the mitochondrial membrane was reduced.

In one aspect, the present invention is directed to a functional food composition for enhancing brain or cognitive function, comprising a black bean extract or a fraction thereof, which comprises 15-25 wt % of delphinidin-3-glucoside, 65-80 wt % of cyanidin-3-glucoside and 5-10 wt % of petunidin-3-glucoside.

The inventive composition for enhancing brain or cognitive function encompasses all forms, including functional foods, nutritional supplements, health foods or food additives, which comprise a component effective in treating or preventing neurodegenerative brain diseases. Also, the inventive composition for enhancing brain or cognitive function can be prepared in various forms according to any conventional method known in the art. For example, a health functional food can be prepared by formulating the black bean extract in the form of tea, juice or drink. Alternatively, the black bean extract can be formulated in the form of granules, capsules or powders, but the forms in which the black bean extract can be formulated are not limited to the above examples.

The health functional food of the present invention may comprise additional additives which are not specifically limited. Preferred examples of foods to which the inventive extract comprising anthocyanins may be added include beverages (including alcoholic beverages), fruits and processed foods thereof (e.g., canned fruits, bottled fruits, jam, marmalade, etc.), fishes, meats and processed foods thereof (e.g., ham, sausage, corned beef, etc.), breads and noodles (e.g., udon, soba (buckwheat noodle), ramen (instant noodle), spaghetti, macaroni, etc.), fruit juices, drinks, cookies, yeot (Korean traditional taffy), dairy products (e.g., butter, cheese, etc.), edible vegetable fats and oils, margarines, vegetable proteins, retort foods, frozen foods, various seasonings (e.g., soybean paste, soy sauce, sauce, etc.), and the like.

The intake of the composition of the present invention is not specifically limited, but may be suitably selected depending on the type of formulation and the age, weight and condition of the user or patient to be administered with the composition.

In another aspect, the present invention is directed to a method for preparing the above composition for preventing or treating neurodegenerative brain diseases, comprising: a) extracting a black bean with water, an organic solvent or a mixed solvent thereof to obtain a black bean extract; b) fractionating the obtained extract with water or a non-polar organic solvent to obtain a fraction; and c) isolating and purifying delphinidin-3-glucoside, cyanidin-3-glucoside and petunidin-3-glucoside from the fraction.

The composition of the present invention can be prepared by chromatography in which components are separated by partitioning between stationary and mobile phases. The stationary phase may be a solid, a liquid present on solid, or a gel and may be packed in a column, or covered on a layer or spread like a film. Chromatographic phase is a general term for various types of stationary phases. Meanwhile, the mobile phase may be gas or liquid. In this method, the components of a mixture are separated from each other on the basis of the difference in mobility between the components during passage through the column. This separation process is based on partitioning of components between the mobile and stationary phases, adsorption, ion exchange, and the difference in size between the components. The degree of interaction of a solute with the mobile or stationary phase depends on the physical and chemical properties of the solute, and polarity can have the greatest effect thereon. Polarity is created by a permanent or induced dipole, a London dispersion force or the like and is influenced by the relative mass of a solvent or a solute.

Methods of separating material is by chromatography are largely classified into four categories: adsorption, partition, ion exchange, and exclusion. Also, the methods are divided, according to the type of mobile phase, into liquid chromatography (LC) and gas chromatography (GC).

Liquid chromatography is adsorption chromatography which uses a liquid mobile phase and a solid stationary phase. An adsorbent which is used in the adsorption chromatography is made mainly of silica, alumina, molecular sieve, porous silica or the like, and this material is packed in a column, and components are adsorbed onto the adsorbent and then eluted with the mobile phase. Thin layer chromatography (TLC) is typical liquid chromatography. In the thin layer chromatography, a material having a shape like one obtained by cutting the cross-section of a tube-shaped column and spreading the cut column is used, and silica gel as an adsorbent is uniformly applied to the surface of the material. The silanol group ($\equiv$Si—OH) of the silica gel acts as an active group, and adsorption is performed by the interaction (such as hydrogen bond) between a sample component and the silanol group. In other words, the interaction of the sample molecule with the stationary phase varies depending on the polarity and steric structure of the sample molecule. A component (e.g., oil or an aromatic compound) that easily dissolves in an organic solvent is easily separated by liquid chromatography, but a polar sample (e.g., glucose or fructose) is not easily separated by liquid chromatography.

GLC and GSC which separate a volatile material by passing gas through the mobile phase with the mobile phase are together referred to as gas chromatography (GC). GC can be considered as the superior method among all chromatographic methods. GC can easily separate a material, which cannot be substantially separated or is very difficult to isolate by other chromatographic methods.

Preferably, the anthocyanin-based compounds of the present invention have a cationic aglycone nucleus, and cationic compounds including anthocyanins can be separated from non-ionic compounds using cation exchange resin. The separated cationic compounds can be subjected to size exclusion chromatography to separate anthocyanin-based compounds from anthocyanin oligomers, and then subjected to reverse-phase chromatography using a C18 Sep Pak column, thereby obtaining a fraction comprising 15-25 wt % of delphinidin-3-glucoside, 65-80 wt % of cyanidin-3-gluco side and 5-10 wt % of petunidin-3-glucoside, which is effective in treating and preventing neurodegenerative brain diseases.

Hereinafter, the present invention will be described in further detail with reference to examples. It is to be understood, however, that these examples are for illustrative purposes and are not intended to limit the scope of the present invention.

Example 1

Separation and Purification of Anthocyanins from Black Bean

Black bean hulls were extracted in a 1% HCl-MeOH solvent, and the extract was treated with cation exchange resin such as Amberlite XAD 7 to separate a cationic component including anthocyanins from non-ionic compounds. Then, to remove nonionic water-soluble and non-polar substances, the cationic component was eluted in 1% HCl-MeOH, thereby obtaining an ionic substance including anthocyanins. In the second step, the ionic substance was subjected to size exclusion chromatography using a column packed with Sephadex LH20 in a mixed solvent of 1% HCl-MeOH/water, and then subjected to reverse-phase chromatography using a C18 Sep Pak column, thereby obtaining ca fraction comprising 15-25 wt % of delphinidin-3-glucoside, 65-0 wt % of cyanidin-3-glucoside and 5-10 wt % of petunidin-3-glucoside.

Example 2

Preparation of Test Animals

Mature male Sprague-Dawley rats (n=16, 2-month-old, weighed 250-280 g) and aged male Sprague-Dawley rats (n=8, 6-month-old, weighed 350-380 g) were housed at a temperature of 20~23° C. with a 12-light/12-hr dark cycle (light: 08:00-20:00) while the animals were allowed access to feed and water ad libitum. The mature rats were divided into two groups: a control group (n=8), and an Alzheimer's disease-induced animal model group (n=8). The aged rats were used as a natural neurodegenerative group. Each of the groups was divided into two subgroups, and one subgroup was fed with tap water and the other subgroup was fed with the anto-cyanins obtained in Example 1.

Example 3

Administration of β-Amyloid (1-42)

In order to make an Alzheimer's disease-induced animal model, β-amyloid (1-42) protein (Sigma-Aldrich, Inc.) was dissolved in distilled water (5 μg/μl) and incubated for 37° C. Immediately before injection, the animals were anesthetized with 50 mg/ml of ketamine and 20 mg/ml of Rompun, and then the area to be administered was exposed. Using a Hamilton syringe attached to a Stereotoxic instrument, 10 μg/2 μL of β-amyloid solution was injected into the test group at a hippocampal area (AP=−4.8 mm; L=3.5 mm, H=4 am), and the same amount of distilled water was injected into the control group at the same position. After surgery, each of the animal groups was divided into two subgroups for administration of anthocyanins and observed for 10 days.

Example 4

Examination of Induction of Alzheimer's Disease (EEG (Electroencephalogram) Study)

Figure 2A:
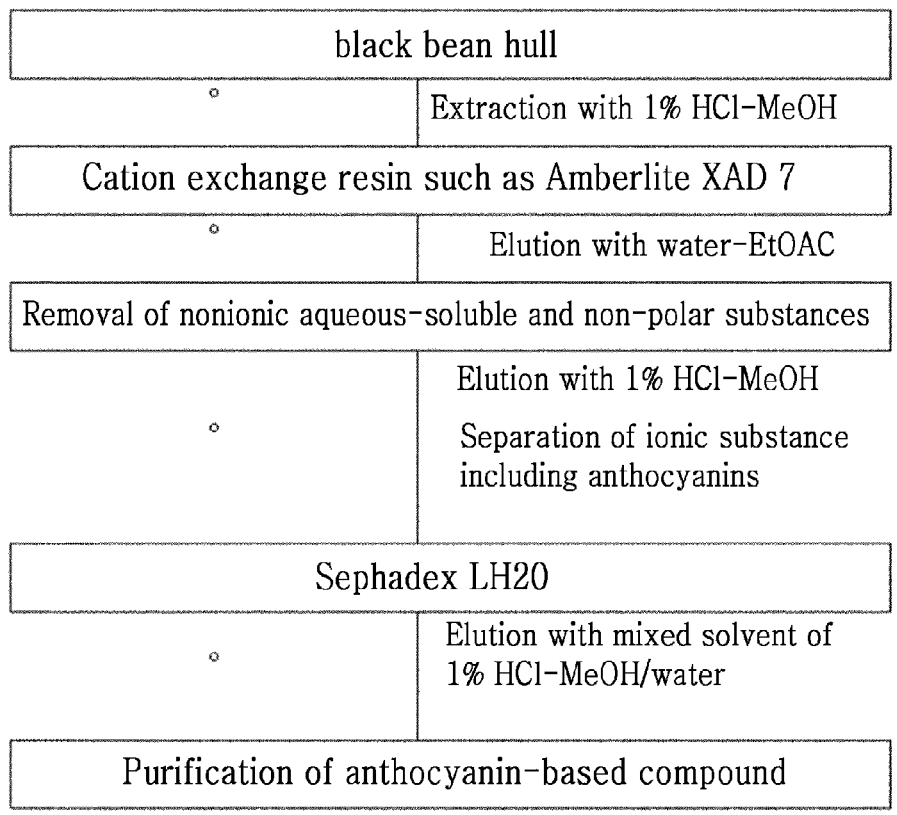
FIG. 2a is a schematic diagram showing a process of purifying an anthocyanin-based compound according to the present invention.

In order to select animals having an Alzheimer's disease induced by injection of β-amyloid (1-42), EEG (LAXTHA, LXEJ 108) was measured. Specifically, amplified signals were measured at 250 Hz for 5 minutes using a modification of the method of R. Ganguly and D. Guha (2008), and animals showing a significant decrease in alpha waves were selected as Alzheimer's disease-induced animals (FIG. 2b).

Example 5

Anthocyanin Treatment

In order to examine whether neuronal cells damaged by induction of Alzheimer's disease and neuronal cells degenerated by natural aging can be regenerated, each of the groups was administered with the anthocyanin fraction which had been extracted and purified from the black beans in Example 1. Specifically, 0.12 mg/ml of the anthocyanin fraction was dissolved in tap water, and the test subgroup divided from each of the control group, the Alzheimer's disease-induced group and the aged rat group was administered orally with 0.48 mg/kg of the anthocyanin solution once a day for 40 days, and the control subgroup was administered orally with tap water once a day for 40 days.

Example 6

Tissue Reparation

To prepare slide tissue samples, the rats of each group were anesthetized with ethyl-ether, and the arteries were fixed in 4% NBP (prepared in 0.1M PBS, 5 ml/min, 100 ml). Then, the brains were extracted and fixed again in 4% NBP (4° C.) for 3 days. Then, the brains were dehydrated in 20% sucrose solution at 4° C. for 3 days and frozen in O.C.T coimpound (A.O., USA), after which the portions including the cortex and the hippocampus were cut to a thickness of 14 μm in the coronal planes (Leica cryostat CM 3050C, Germany). The sections were mounted on gelatin-double-coated slides and stored −80° C. until use. To prepare protein samples, the rats of each group were anesthetized with 50 mg/ml of ketamine and 20 mg/ml of Rompun, and then the brains were extracted and separated quickly into portions on ice. The separated portions were frozen rapidly in liquid nitrogen and stored at −80° C. until use.

Example 7

Nissl, FJB (Fluoro-Jade B) and PI (Propidium Iodide) Staining

After administration of the anthocyanins for 40 days, the structure and degree of death of the neuronal cells were examined by Nissl staining and FJB/PI staining. For Nissl staining, the slides were dried at room temperature for 3 hours and then washed twice with PBS, and crystal violet dye was added to the slides which were then allowed to stand at room temperature for 3 minutes. Then, the slides were washed water and dehydrated with alcohol series (50%, 70%, 90%, 95% and 100%) for 3 minutes, after which the slides were washed with xylene and observed with an optical microscope. For FJB/PI staining, the slides were dried in the same manner as described above, after which the slides were immersed in 0.1% sodium hydroxide and 80% ethanol for 5 minutes and then in 70% ethanol for 2 minutes, followed by washing with water. Then, the slides were immersed in 0.06% potassium permanganate solution for 10 minutes, followed by washing with water. Then, the slides were immersed in 0.1% acetic acid and 0.01% FJB (Chemicon Int., USA) for 20 minutes, thereby staining the slides. Then, the slides were washed twice with distilled water, followed by drying at room temperature for 10 minutes. Then, each of the slides was immersed in a solution of 1 μg/ml PI in PBS and stirred on a stirrer at room temperature for 20 minutes to stain the nucleus. Then, the slides were washed twice with PBS solution for 10 minutes, covered with mounting solution and imaged using a FITC/PI filter in a Confocal microscope (Olympus, Japan), followed by photography with an image system video camera.

Figure 6A:
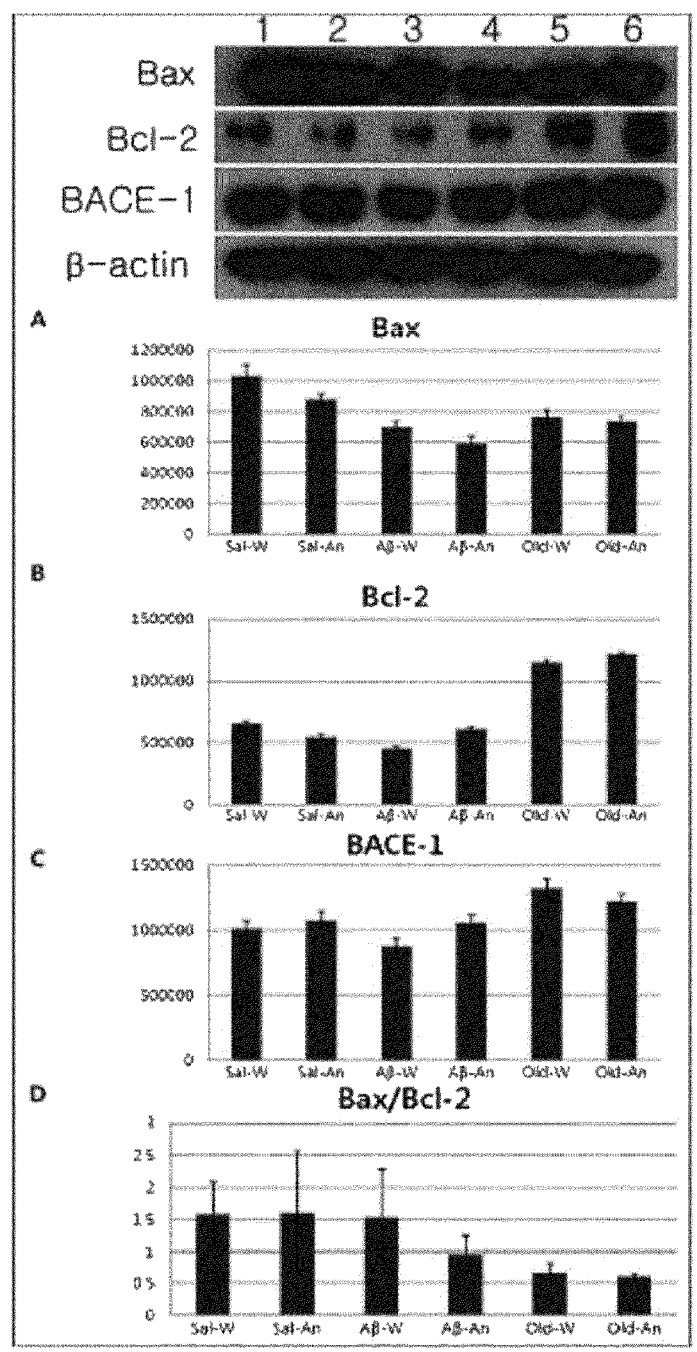
FIG. 6a shows the results of measuring the expression levels of Bax, Bcl-2 and BACE-1 proteins in the hippocampus of dementia-induced rats and aged rats. A: Bax; B: Bcl-2; C: BACE; 1. Sal-W: saline together with tap water; 2. Sal-An: saline together with anthocyanins; 3. Aβ-W: Aβ together with tap water; 4. Aβ-An: Aβ together with anthocyanins; 5. Old-W: tap water administered to aged rats; 6. Old-An: anthocyanins administered to aged rats.
Figure 6B:
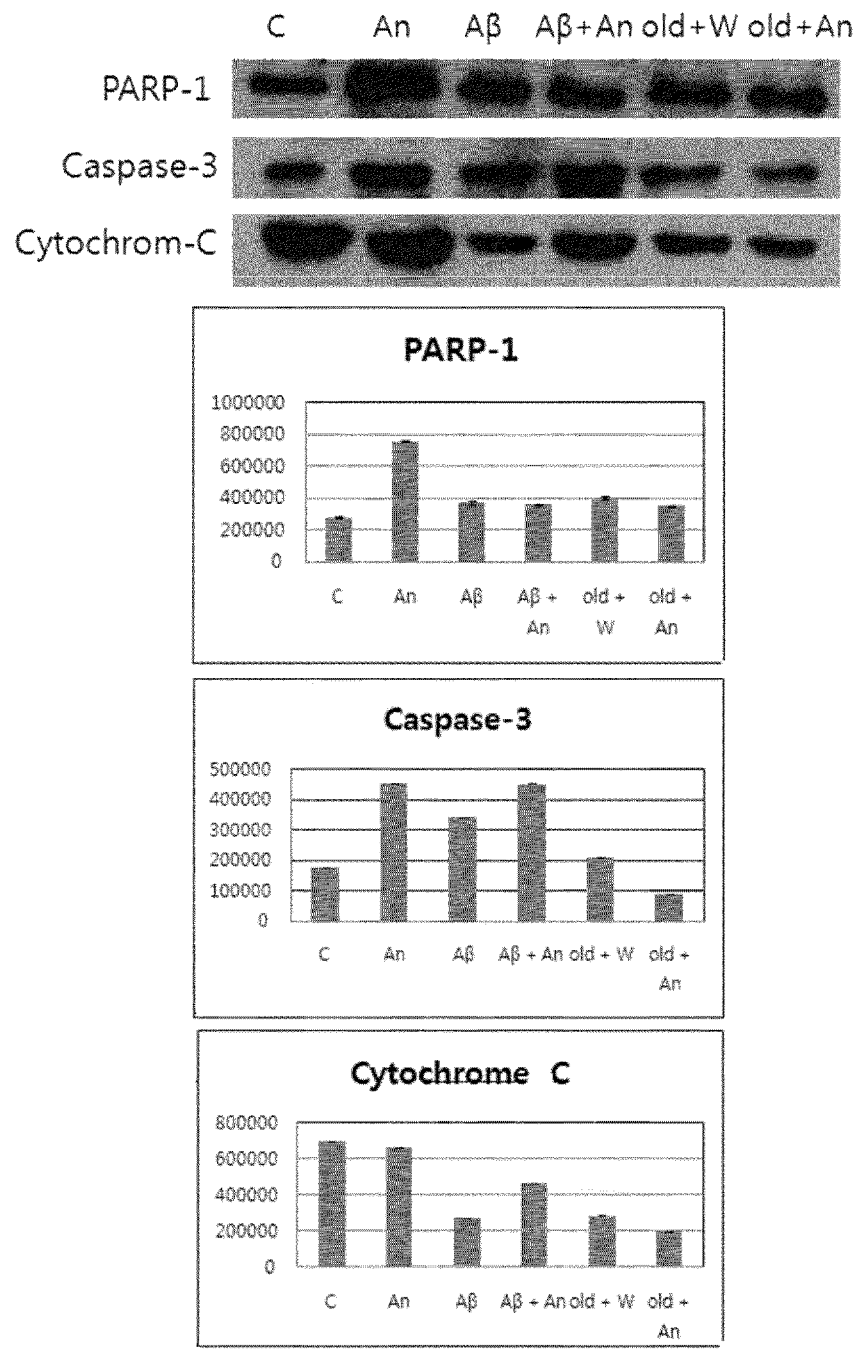
FIG. 6b shows the results of examining the changes in PARP-1, caspase-3 and cytocrom-C proteins involved in cell death in the hippocampus of dementia-induced rats and aged rats. It can be seen that dementia was selectively inhibited in the group administered with anthocyanins.
Figure 6E:
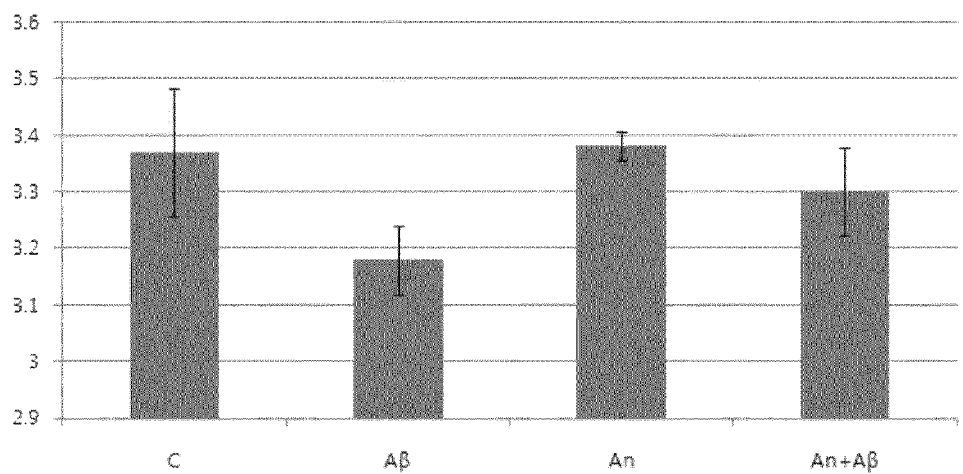
FIG. 6e shows the results of an MTT assay carried out to measure the cytotoxicity of HT22 cells in dementia-induced rats treated with beta-amyloid together with anthocyanins. Aβ (25-35): 40 uM; anthocyanins: 0.2 mg/ml for 24 hr.
Figure 6F:
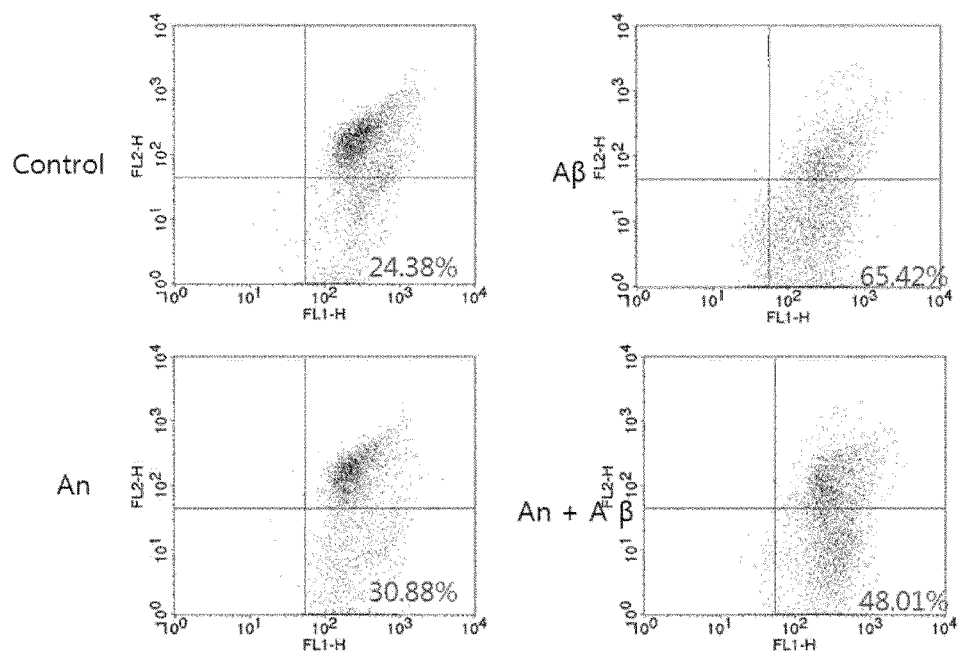
FIG. 6f shows the results of JC-1 analysis carried out to measure the chance in the mitochondrial membrane in dementia-induced rats treated with beta-amyloid together with anthocyanins. Aβ (25-35): 40 uM; anthocyanins: 0.2 mg.ml for 24 hr.
Figure 7:
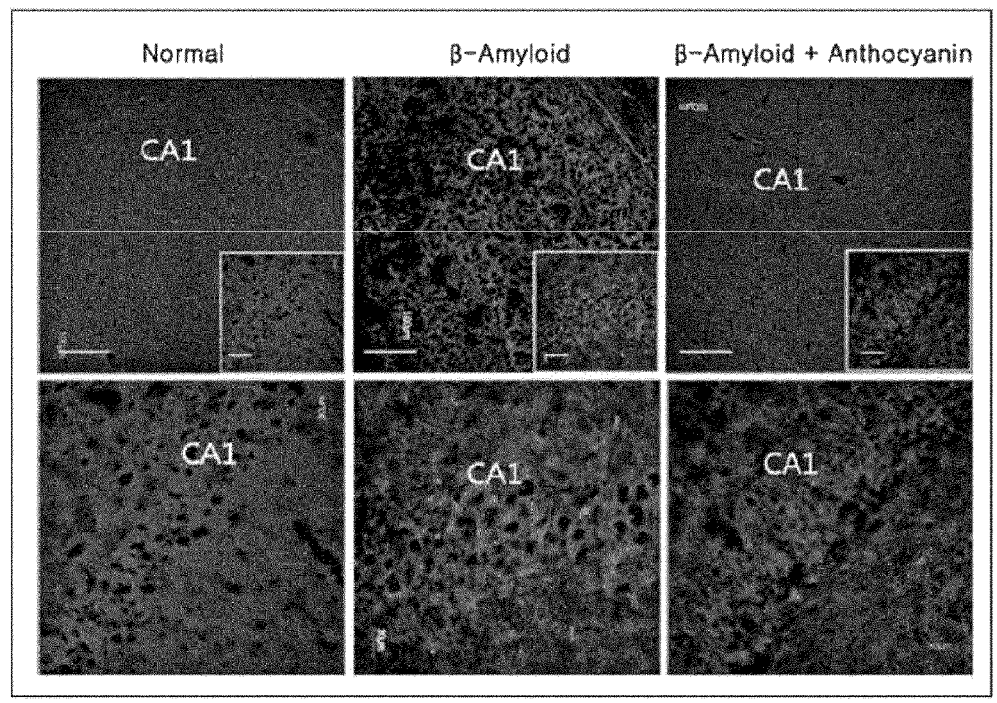
FIG. 7 shows the results of examining neurological cell death in the hippocampal CA1 area by FJB staining (the photographs in the second line are enlarged photographs of the square portions shown in the first line).
Figure 8:
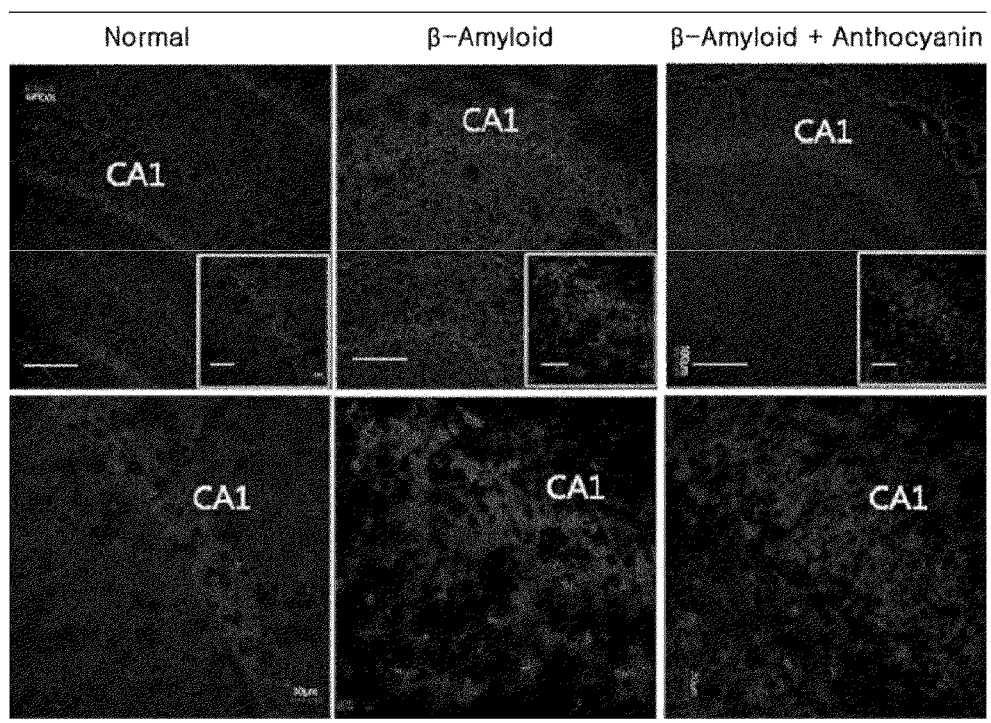
FIG. 8 shows the results of examining cell death in the hippocampal CA1 area by PI staining.

In the results of staining with FJB that binds to dead neurons to show a light green color which indicates the degree of cell death, the normal group showed no light spot, but the Aβ-treated group showed very light green spots. However, spots in the group treated with the anthocyanins together with Aβ decreased compared to those in the Aβ-treated group, suggesting that neurons in the CA1 area of the hippocampus were protected from cell death (FIG. 7). The results of staining the hippocampal CA1 area with PI indicated patterns similar to those in FIG. 6, suggesting that the cell death induced by Aβ treatment and the cell death induced by necrosis could be inhibited by the anthocyanins (FIG. 8).

Figure 9:
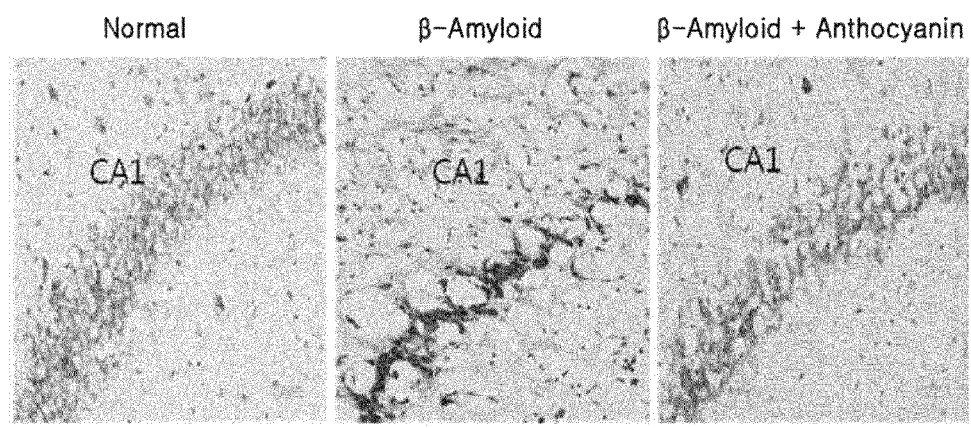
FIG. 9 shows the results of observing the morphology of neuronal cells in the hippocampal CA1 area by Nissle staining.

In order to observe any neurological change in the hippocampal CA1 area of each treated group, Nissl staining was performed. Nissl staining makes it possible to observe neurological changes by staining neurons, particularly Nissl substance, neuroglial nuclei, blood vessels, lymphatic vessels, and connective tissues. As a result, in the normal groups, neurons were mostly normal, whereas in the group treated with Aβ, the number of neurons was significantly decreased compared to those in the normal group, and additionally the neurons were shrunk. However, in the group treated with the anthocyanins together with Aβ, the number of neuronal cells increased compared to the group treated with Aβ alone, and the shape thereof was also close to the normal shape (FIG. 9).

Example 8

Western Blotting

In order to examine the induction of Alzheimer disease and the degree of degeneration of neuronal cells at the protein level, the expression levels of BACH-1, Bax and bcl-2 were measured by Western blotting. As a control, the expression level of β-actin was measured. Specifically, for protein extraction, tissue was homogenized in PBS using a tissue homogenizer, and then centrifuged twice at 12,000 rpm and 4° C. for 15 minutes, thereby obtaining the total protein. The total protein was quantified using Bio-rad protein assay buffer according to the Bradford method, and 30 g of the protein was loaded onto 10% SDS-polyacrylamide gel (30% acrylamide, 1% Bis, 1M Tris, 10% APS, TEMED). The gel was transferred to a PVDF membrane (25 V, 300 mA, 30 min) using fast semi-dry transfer buffer (Thermo Scientific) and reacted with each of primary antibody rabbit-derived-anti-BACE-1 (1:1000, 18 hr, 4° C., Sigma), anti-Bax (1:500, Santa Cruz), anti-Bcl-2 (1:500, Santa Cruz) and anti-β-actin (1:1000, Sigma), followed by reaction with secondary antibody HRP-conjugated goat anti-rabbit IgG (1:1000, RT, 90 min, Bio-Rad). For detection, ECL-detecting reagent (Amersham Biosciences) was used, and the membrane was exposed to an X-ray film and scanned using a scanner and analyzed densitometrically using Sigmagel version 1.0 (Fandel Scientific, USA).

Bax and Bcl-2 are cell death regulatory proteins belonging to the Bcl-2 family. Bax acts to induce cell death, and Bcl-2 acts as a signal to inhibit cell death. As described above, BACE-1 acts to cleave β-amyloid precursor protein (APP) to form amyloid-βprotein (Aβ).

Figure 5A:
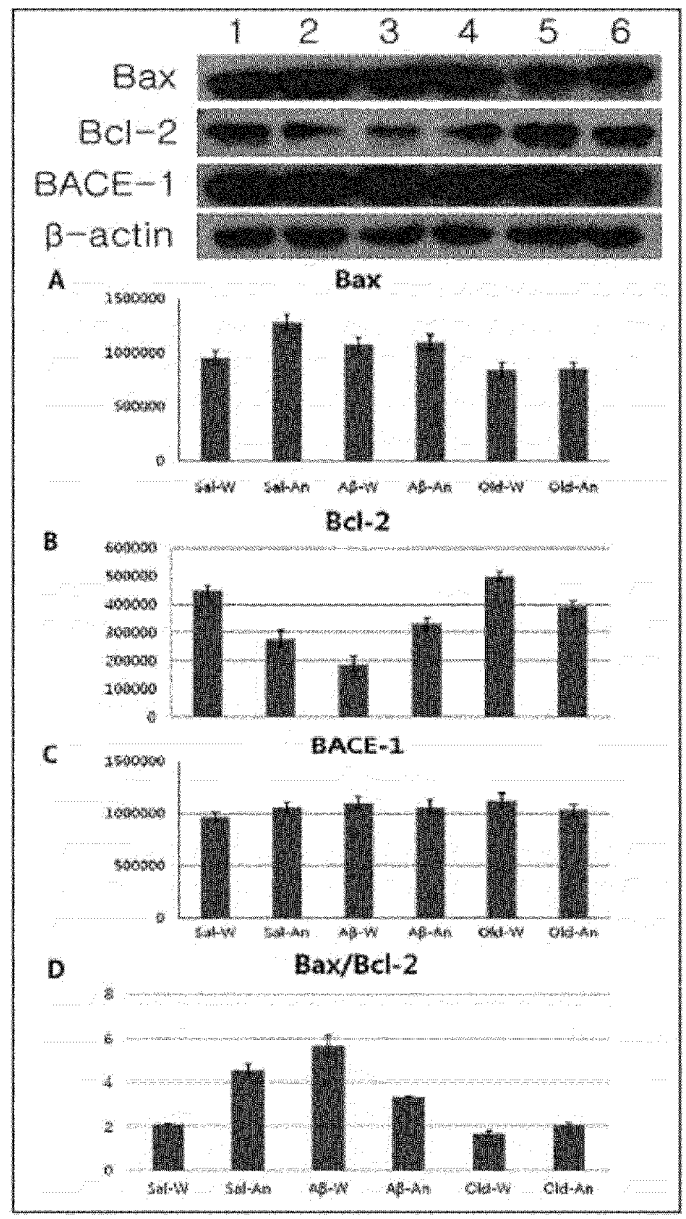
FIG. 5a shows the results of measuring the expression levels of Bax, Bcl-2 and BACE-1 proteins in the cortices of dementia-induced rats and aged rats after treatment with anthocyanins. A: Bax; B: Bcl-2; C: BACE; 1. Sal-W: saline together with tap water; 2. Sal-An: saline together with anthocyanins; 3. Aβ-W: Aβ together with tap water; 4. Aβ-An: Aβ together with anthocyanins; 5. Old-W: tap water administered to aged rats; 6.Old-An: anthocyanins administered to aged rats.

As a result, in the cortex of the brain of the normal rat group (control group) and the aged rat group, the expression of Bax was increased or not changed by anthocyanin treatment, whereas in the dementia-induced rats, the expression of Fax was slightly increased and the expression of Bcl-2 was significantly increased by anthocyanin treatment. The results of analysis of the Bax/Bcl-2 ratio indicated that the anthocyanins regulated cell death and inhibited neuronal cell death in the dementia-induced rats. In addition, the expression of BACE-1 protein in the dementia-induced model and the aged animal model was slightly decreased by the anthocyanins (FIG. 5a).

Figure 5B:
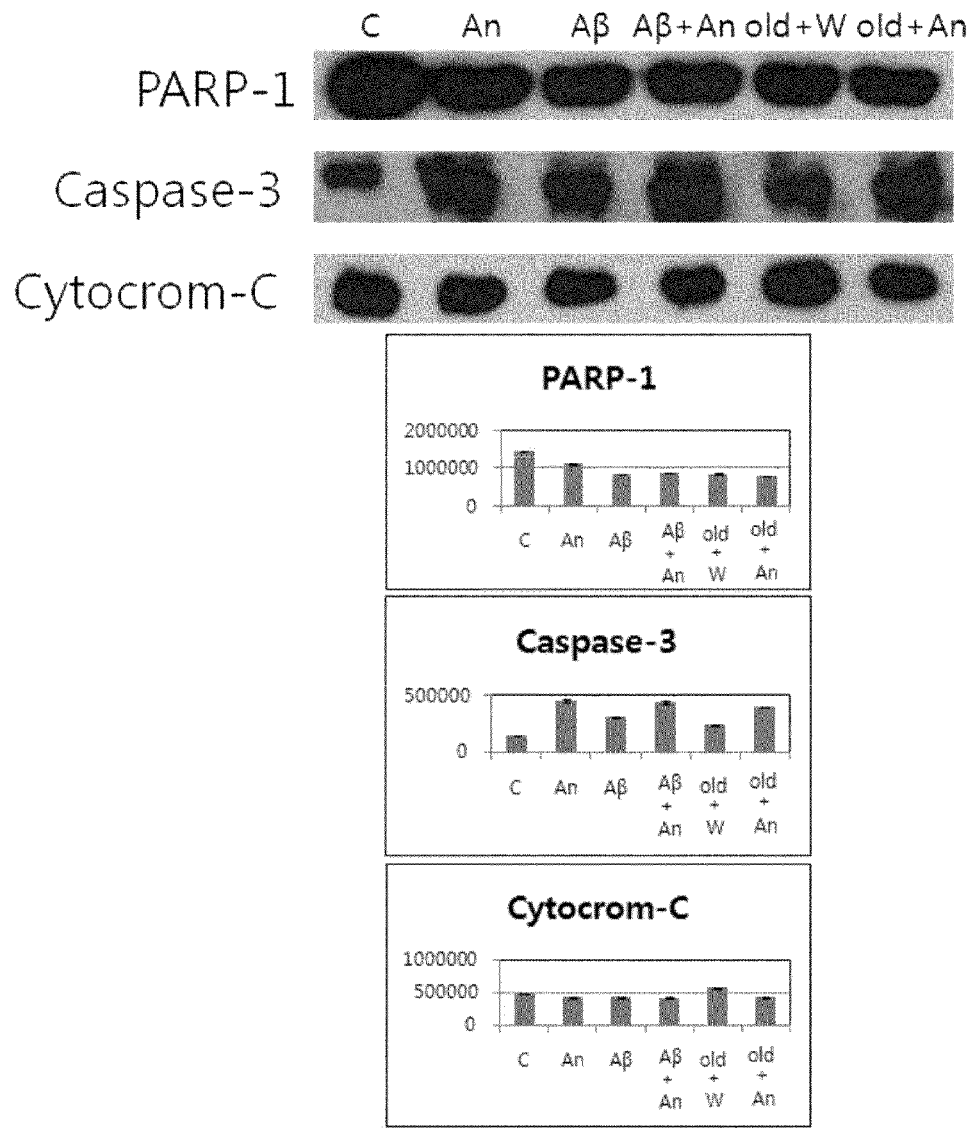
FIG. 5b shows the results of examining the changes in PARP-1, caspase-3 and cytocrom-C involved in the cerebral cortices of dementia-induced rats and aged rats. It could be seen that dementia was selectively inhibited in the group administered with antocyanins. C: control; An: anthocyanins; Aβ: β-amyloid; Aβ-An: Aβ together with anthocyanins; Old-W: Lap water administered to rats; Old-An: anthocyanins administered to aged rats.

Furthermore, the changes in PARP-11, caspase-3 and cytochrome-C proteins involved in cell death in the cerebral cortex of the beta-amyloid-induced dementia rat model and the aged rat model were examined. As a result, it could be seen that dementia in the group administered with the anthocyanins was selectively inhibited (FIG. 5b).

Figure 5C:
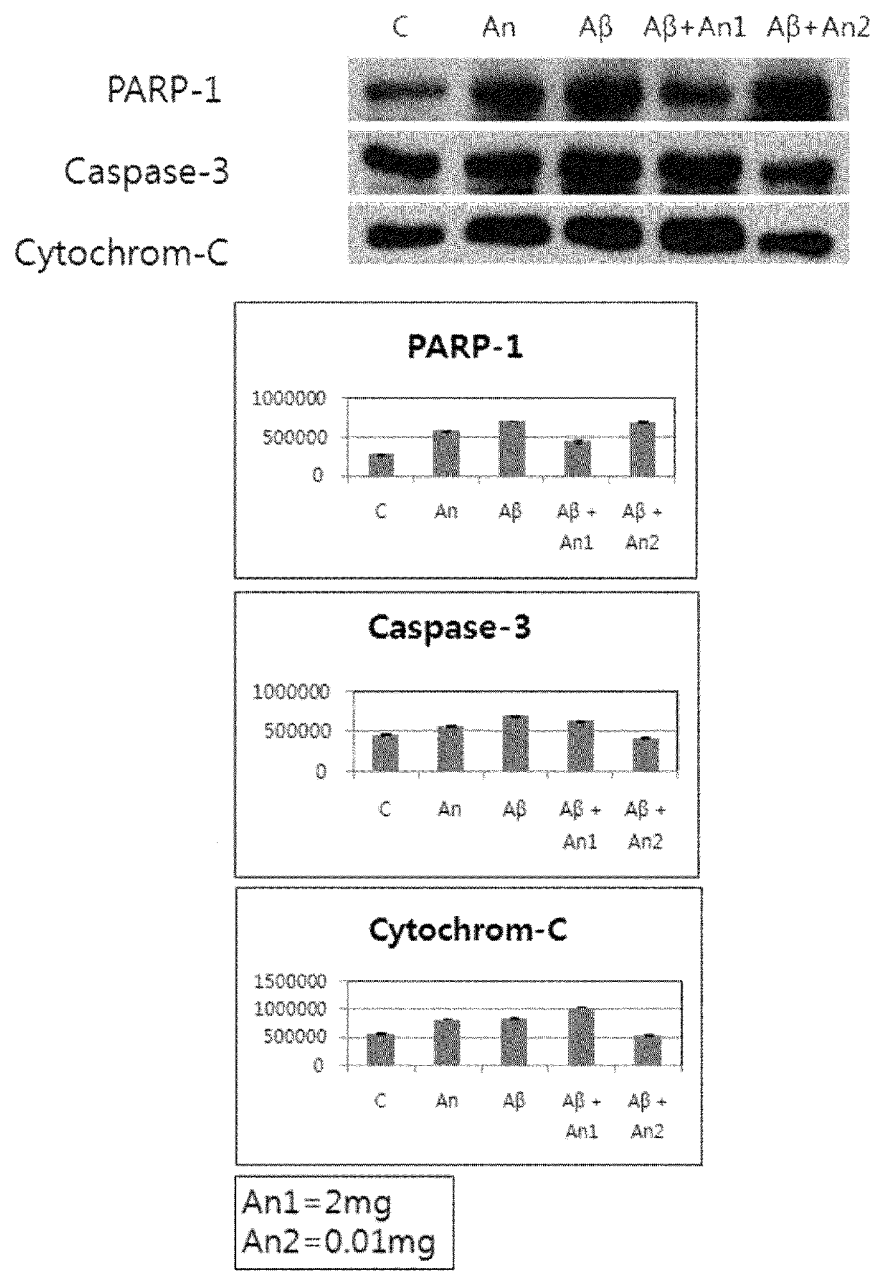
FIG. 5 shows the results of examining the changes in PARP-1, caspase-3 and cytocrom-C proteins involved in cell death in the cerebral cortex of dementia-induced rats as a function of the concentration of anthocyanins. It was observed that cell death was much more inhibited in the group administered with 2 mg of anthocyanins. C: control; An: anthocyanins; Aβ: β-amyloid; Aβ+An1: Aβ together with 2 mg of anthocyanins; Aβ+An2: Aβ together with 0.01 mg of anthocyanins.

Moreover, the changes in PARP-1, caspase-3 and cytochrome-C proteins involved in cell death in the cerebral cortex of the beta-amyloid-induced dementia rat model and the aged rat model were examined as a function of the concentration of anthocyanins administered. As a result, it could be seen that dementia in the group administered with 2 mg of the anthocyanins was selectively inhibited (FIG. 5c).

Also, the changes in PARP-1, caspase-3 and cytochrome-C proteins involved in cell death in the hippocampal area of the beta-amyloid-induced dementia rat model and the aged rat model were examined. As a result, it could be seen that dementia in the group administered with the anthocyanins was selectively inhibited (FIG. 6b).

Further, the changes in PARP-1, caspase-3 and cytochrome-C proteins involved in cell death in the hippocampal area of the beta-amyloid-induced dementia rat model and the aged rat model were examined as a function of the concentration of anthocyanins administered. As a result, it could be seen that dementia in the group administered with 2 mg of the anthocyanins was selectively inhibited (FIG. 6c).

In addition, the changes in Bax, Bcl-2 and BACE-1 proteins involved in cell death in the hippocampal area of the beta-amyloid-induced dementia rat model and the aged rat model were examined as a function of the concentration of anthocyanins administered. As a result, it could be seen that cell death in the group administered with 2 mg of the anthocyanins was much more inhibited (FIG. 6d).

Example 9

Observation of Changes in BACE-1 Protein, Cell Proliferation, Cytotoxicity and Mitochondrial Membrane in Embryonic Cortical Neurons after Treatment with Anthocyanins BACE-1 is an enzyme that cleaves beta-site APP (β-amyloid precursor protein) to form β-amyloid protein (Aβ). Thus, an increase in BACE-11 protein means an increase in the deposition of Aβ, and it is a potent substance causing dementia and is an index of dementia diagnosis. Accordingly, the present inventors carried out the following test in order to observe a change in the BACE-1 protein.

For an in vitro test in differentiating neuronal cells, the cerebral cortical cells of white rat embryos (n=10) 17.5 days old were primarily cultured. Specifically, cortical tissue extracted by a surgical operation using a stereoscopic microscope was treated with 0.25% trypsin-EDTA for 20 minutes and dissociated in calcium- and magnesium-free HBSS (Hank's balanced salt solution) (pH 7.4), followed by centrifugation. The pellets (embryonic cortical cells) were collected and placed on a cell culture plate precoated with polylysine (0.02 g/l) and a chamber slide ($1 \times 10^6$ cells/ml). The medium was composed of DMEM (Dulbecco's modified Eagle medium), 10% heat-inactivated bovine serum, 1 mM pyruvate, 4.2 mM sodium hydrogen carbonate, 20 mM HEPES, 0.3 g/l bovine serum albumin, 50 U/ml penicillin and 50 mg/l streptomycin. Culture of the cells was carried out in a 5% $CO_2$ incubator at a humidity of 95% and a temperature of 37° C. Neuroglia cells were inhibited by a medium containing 100 μM cytosine β-D-arabino furanoside for 12 hours. After 3 days, the cortical neuronal cells were divided into a control group, a group treated with beta-amyloid, a group treated with anthocyanins, and a group treated with beta-amyloid and anthocyanins. The cells were treated with 20 mg/ml of anthocyanins and 10 μM of beta-amyloid by in vitro incubation at 37° C. for 48 hours, and then collected, after which the expression of BACE-1 in the cells was measured by Western blotting similar to that in Example 8. In addition, the cell number was increased and was observed with a microscope.

Figure 3:
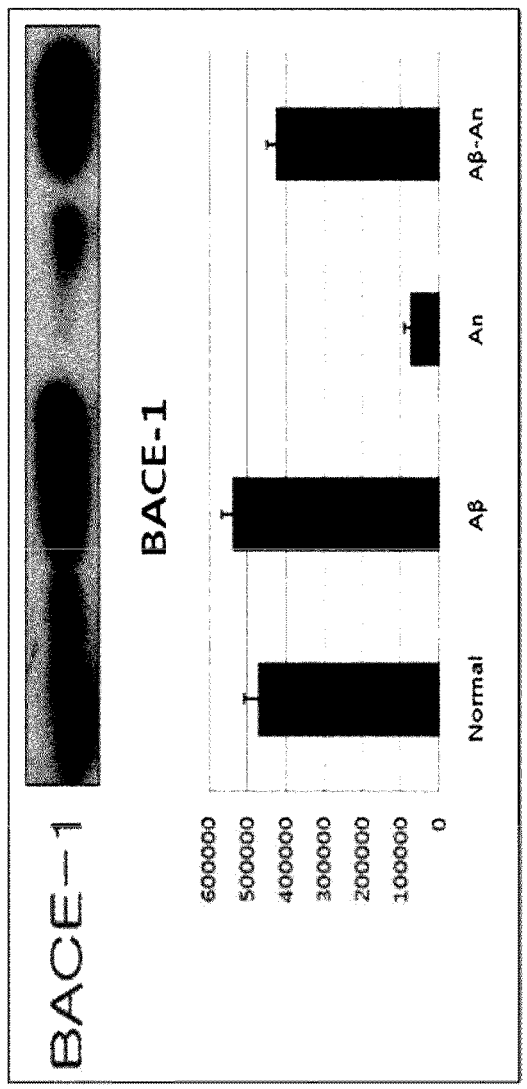
FIG. 3 shows the results obtained by primarily culturing the cortical cells of white rat embryos 17.5 days old, treating the cultured cells with 2 mg/0 ml of anthocyanins and 10 uM of β-amyloid for 48 hours, and then measuring the expression of BACE-1 protein in the collected cells. Normal: control group treated with Aβ 25-35; An: treated with anthocyanins; Aβ-An: treated with Aβ (25-35)+ anthocyanins.

As a result, the expression level of BACE-1 in the Aβ-treated group was significantly higher than that in the control group, and the expression level of BACE-1 in the group treated with the anthocyanins alone was significantly lower than those in other groups. In addition, the expression level of BACE-1 in the group treated with the anthocyanins together with Aβ was also lower than that in the control group. Such results suggest that the anthocyanins of the present invention have the effect of inhibiting neurodegeneration (i.e., dementia) in the embryonic cortical neuronal cells of white rat (FIG. 3).

For an in vitro test in differentiating neuronal cells, the cerebral cortical cells of white rat embryos (n=10) 17.5 days old were primarily cultured. Cortical tissue extracted by a surgical operation using a stereoscopic microscope was treated with 0.25% trypsin-EDTA for 20 minutes. As a result, the proliferation of the cells in the group treated with beta-amyloid was significantly decreased, whereas the formation of Aβ in the group treated with the anthocyanins alone (FIG.

Figure 4:
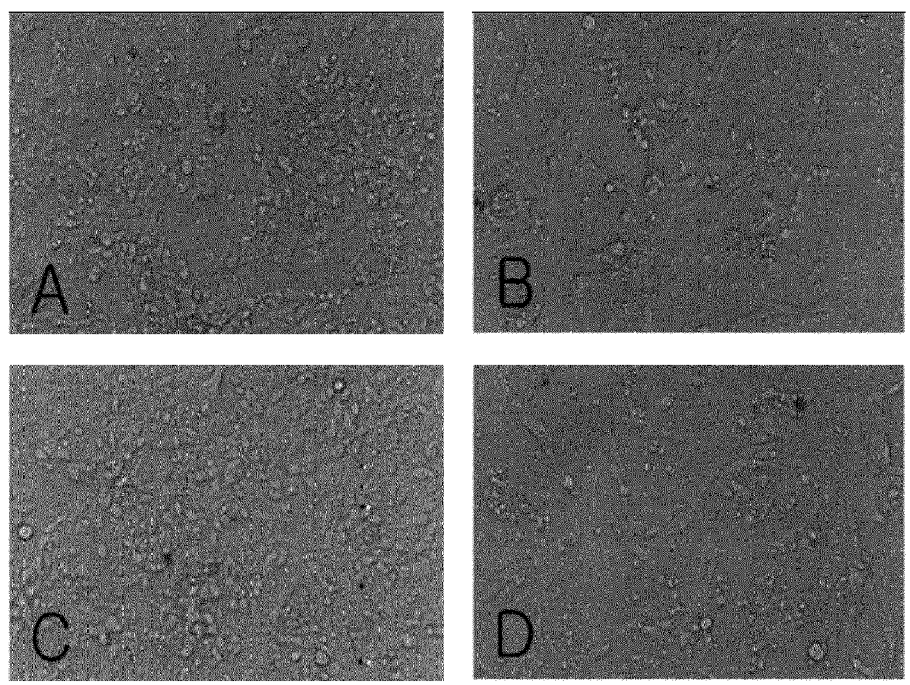
FIG. 4 shows the results obtained by primarily culturing the cortical cells of white rat embryos 11.7.5 days old, treating the cultured cells with 2 mg/10 ml of anthocyanins and 10 uM of β-amyloid for 48 hours, and then examining the cell proliferation which resulted from treatment with Aβ and anthocyanins. A: control group; B: treated with Aβ; C: treated with anthocyanins; D: treated with Aβ+ anthocyanins.

4C) was inhibited, suggesting that the proliferation of the cells was increased. The number of the cells observed in the group treated with the anthocyanins together with Aβ (FIG. 4D) was larger than that in the group treated with beta-amyloid alone. Such results suggest that the anthocyanins can inhibit cell death caused by Aβ treatment (FIG. 4).

In the hippocampal areas of all the normal rat group (control group), the dementia-induced rat group and the aged model rat group, the expression of Bax was reduced by anthocyanin treatment. Also, the expression of Bcl-2 was increased in the dementia-induced group and the aged rat group, suggesting that the anthocyanins had the effect of inhibiting neuronal cell death in all the groups. In addition, it was shown that the expression of BACE-1 protein was inhibited by the anthocyanins in the aged rat model group only. Thus, it could be seen that the effect of the anthocyanins on the protection of neuronal cells was more significant in the hippocampus and was higher in the dementia-induced group and the aged rat model than in the normal rat group (FIG. 6a).

Further, the cytotoxicity of HT22 cells caused by beta-amyloid treatment in the case of anthocyanin treatment was analyzed by an MTT assay. As a result, it was shown that cytotoxicity could be reduced in the group treated with anthocyanins (FIG. 6e).

In addition, the change in the mitochondrial membrane caused by beta-amyloid treatment in the case of anthocyanin treatment was analyzed by JC-1. As a result, it was shown that the change in the mitochondrial membrane could be reduced in the group treated with the antocyanins (FIG. 6f).

The above-described results indicate that the anthocyanins of the present invention inhibited neuronal cell death and that this inhibition was more significant in the dementia-induced model and the aged model than in the control group, suggesting that the anthocyanins are effective in ameliorating dementia and increasing memory function.

INDUSTRIAL APPLICABILITY

As described above, the black bean extract (anthocyanins) that is contained in the composition of the present invention has the effects of inhibiting neuronal cell death induced by aging and β-amyloid in the cortex and hippocampus of the brain and of regenerating neuronal cells. Thus, it can be used as a pharmaceutical formulation and food composition for treating or preventing neurodegenerative brain diseases.

The invention claimed is:

1. A method for treating neurodegenerative brain disease, comprising administering an effective amount of a composition consisting essentially of 15-25 wt % of delphinidin-3-glucoside, 65-80 wt % of cyanidin-3-glucoside, and 5-10 wt % of petunidin-3-glucoside; and, optionally, a pharmaceutically acceptable carrier, to a subject in need thereof.

2. The method of claim 1, wherein the composition includes the pharmaceutically acceptable carrier.

3. The method of claim 1, wherein the neurodegenerative brain disease is dementia or Alzheimer's disease.

4. The method of claim 1, wherein the neurodegenerative brain disease is a disease induced by beta-amyloid protein in brain cells.

5. The method of claim 1, wherein the composition has an effect of protecting neuronal cells.

6. The method of claim 5, wherein the effect of protecting neuronal cells is achieved by reducing a cytoxicity on the neuronal cells.

7. The method of claim 5, wherein the neuronal cells are cerebral cortical or hippocampal neuronal cells.

8. The method of claim 5, wherein the effect of protecting neuronal cells is achieved by inhibiting a change in a mitochondrial membrane of the neuronal cells.

9. The method of claim 5, wherein the effect of protecting neuronal cells is achieved by inhibiting death of the neuronal cells.

* * * * *